US011241316B2

(12) United States Patent
Oksala et al.

(10) Patent No.: US 11,241,316 B2
(45) Date of Patent: Feb. 8, 2022

(54) IMPLANT COATING

(71) Applicant: PICOSUN OY, Espoo (FI)

(72) Inventors: Niku Oksala, Tampere (FI); Marko Pudas, Espoo (FI)

(73) Assignee: PICOSUN OY, Espoo (FI)

( * ) Notice: Subject to any disclaimer, the term of this patent is extended or adjusted under 35 U.S.C. 154(b) by 0 days.

(21) Appl. No.: 16/830,918

(22) Filed: Mar. 26, 2020

(65) Prior Publication Data

US 2020/0306046 A1  Oct. 1, 2020

Related U.S. Application Data

(60) Provisional application No. 62/826,453, filed on Mar. 29, 2019.

(51) Int. Cl.
*A61F 2/28* (2006.01)
*A61B 17/86* (2006.01)

(52) U.S. Cl.
CPC .......... *A61F 2/28* (2013.01); *A61F 2240/001* (2013.01); *A61F 2250/006* (2013.01); *A61F 2310/00958* (2013.01)

(58) Field of Classification Search
CPC ........ A61L 27/34; A61L 29/085; A61L 31/10; A61L 2420/02; A61L 31/16; A61L 27/56; A61L 2430/02; A61L 27/16; A61L 2420/06; A61L 29/16; A61L 2400/18; A61L 2430/12; A61L 31/146; A61L 2430/24; A61L 2420/04; A61L 2420/08; A61L 31/08; A61L 2300/606; A61L 27/28; A61L 29/08; A61F 2002/2817; A61F 2002/2835; A61F 2002/30064; A61F 2002/4007; A61F 2002/4022; A61F 2002/4066; A61F 2002/407; A61F 2002/4649; A61F 2310/00359; A61F 2/28; A61F 2/4014; A61F 2/4059; A61F 2/4081

See application file for complete search history.

(56) References Cited

U.S. PATENT DOCUMENTS

| 2006/0251875 | A1 | 11/2006 | Carlisle et al. | |
|---|---|---|---|---|
| 2013/0053938 | A1 | 2/2013 | Miller et al. | |
| 2014/0086962 | A1* | 3/2014 | Jin | A61L 27/38 424/400 |
| 2015/0175814 | A1* | 6/2015 | Aizenberg | C03C 17/001 428/312.8 |
| 2015/0217096 | A1* | 8/2015 | Piveteau | A61B 17/68 427/2.25 |

(Continued)

FOREIGN PATENT DOCUMENTS

| DE | 2 313 678 A1 | 10/1974 |
|---|---|---|
| EP | 0 295 397 A1 | 12/1988 |
| EP | 0 573 694 A2 | 12/1993 |

(Continued)

OTHER PUBLICATIONS

Extended European Search Report issued in European Patent Application No. 20 165 604.8 dated Aug. 3, 2020.

*Primary Examiner* — Ann Schillinger

(74) *Attorney, Agent, or Firm* — Nixon & Vanderhye

(57) ABSTRACT

A medical implant structure is provided comprising a substrate 10 with at least a first surface and a second surface that surfaces differ from one another with regard to at least one property in relation to biological material.

10 Claims, 1 Drawing Sheet

(56) References Cited

U.S. PATENT DOCUMENTS

2020/0069848 A1* 3/2020 Van Buskirk ............ A61L 31/16

FOREIGN PATENT DOCUMENTS

| EP | 0 573 694 A3 | 12/1993 |
|---|---|---|
| WO | 2012/135107 A2 | 10/2012 |
| WO | 2012/135107 A3 | 10/2012 |
| WO | 2017/023527 A1 | 2/2017 |

* cited by examiner ical implants.

IMPLANT COATING

FIELD OF THE INVENTION

The present invention generally relates to medical endoprostheses. In particular, the invention pertains to an improved endoprosthesis structure with surface modulated properties.

BACKGROUND OF THE INVENTION

Endoprostheses and endoprosthetic systems generally refer to implantable devices and assemblies to remodel and reconstruct skeletal defects, to replace joints and to deal with musculoskeletal disorders. Conventional implantable prostheses are typically made of metals (e.g. titanium and titanium alloys, stainless steel), ceramics, polymers and a combination thereof.

A common problem arising upon utilization of conventional endoprostheses, e.g. all-titanium implants, is that when used at the interface with biological tissue, especially, bone tissue, the implant can adhere too strongly to bone; therefore, it may be challenging or even impossible to be removed.

For example, in certain surgical reconstruction procedures, such as in hip or knee arthroplasty, for example, failure of the implant or excessive wearing of the implant may require a revision procedure, such as revision arthroplasty, accordingly. In some instances, the indication for the revision arthroplasty is loosening of the implant due to aseptic loosening (when the bond between an implant and bone fails in an absence of infection). In such cases, the implant can be removed relatively easily and the only remaining problem is how to fill the bone cavities emerged due to osteolysis. However, sometimes the implant is totally integrated with the bone, especially when the indications include bacterial infection resulting in creating biofilm on the prosthesis, but not necessarily affecting an implant shaft or an interface with the bone; bone fracture; joint instability or a limited range of motion (ROM) after the surgery (e.g. arthroplasty).

In revision surgery aiming at correcting implant failures, dense scar tissue appears around the old prosthesis. To remove such implant, extensive and slow preparative work is required, whereupon scar tissue is removed by surgical intervention and the implant becomes exposed.

In addition of being complex and costly, revision surgery requires significant planning and expertise. The procedure is further characterized with long recovery periods, and often involves an extensive risk of complications and impaired quality of life after the intervention. Ultimately, it may take almost a year to recover from the surgery and the end result is often inferior to primary arthroplasty.

The surgeon has to preserve a balance between good exposure of the implant while avoiding sacrificing the supporting ligaments, muscles and/or bone tissue. In such operations, especially, in the elderly, the problem is that the bone is often osteoprotic and therefore fragile, which results in high probability of wide supporting bone destruction during implant removal. This necessitates filling of the cavities with a cement or bone grafts. The implants used in revision surgery are characterized with extension stems and metal augments enabling strong fixation of the implant into the bone.

In this regard, an update in the field of manufacturing of endoprostheses and/or in modifying the surface properties of said endoprostheses is still desired to address the challenges associated with optimizing bone-to-implant contacts via establishing biological interactions between the implant and the surrounding tissue.

SUMMARY OF THE INVENTION

An objective of the present invention is to solve or to at least alleviate each of the problems arising from the limitations and disadvantages of the related art. The objective is achieved by various embodiments of a medical implant improved in terms of its' surface modulating properties. Thereby, in one aspect of the invention a medical implant structure is provided according to what is defined in independent claim 1.

In embodiment, the medical implant structure comprises a substrate with at least a first surface and a second surface that surfaces differ from one another with regard to at least one property in relation to biological material.

In embodiment, the first surface and the second surface differ from one another in terms of at least one property selected from the group consisting of adhesion, cell growth, biological activity, and toxicity.

In embodiment, the first surface and the second surface are disposed essentially on top of each other. In embodiment, the at least one surface is established by a coating layer. In embodiment, said at least one coating layer is deposited with atomic layer deposition (ALD).

In embodiment, the at least one surface is established by a conformal coating layer. In embodiment, the surface established by the conformal coating layer is deposited over the substrate surface.

In embodiment, the at least one surface is established by a non-conformal coating layer. In embodiment, the at least one surface established by a non-conformal coating layer is deposited over the surface established by the conformal coating layer. In embodiment, the at least one surface established by a non-conformal coating layer is deposited over the substrate surface.

In embodiment, the substrate surface void of any coating layer is oxidized.

In embodiment, the conformal coating layer is established by an Atomic Layer Deposition (ALD) layer.

In an aspect, a joint implant is provided. The joint implant comprises the medical implant structure according to the embodiments.

In an aspect, a method of manufacturing a medical implant structure is provided .

In embodiment, the methods comprises obtaining a substrate and depositing an at least one conformal coating layer onto said substrate, wherein said conformal coating layer is established by an Atomic Layer Deposition (ALD) layer.

In embodiment, the method further comprises depositing a non-conformal coating layer over the surface established by the conformal coating layer.

In embodiment, the method further comprises removal of at least a part of the conformal coating layer deposited over the substrate, whereby at least a part of the substrate surface is rendered exposed, and depositing a non-conformal coating layer over the exposed substrate surface.

Without limiting the scope and interpretation of the patent claims, certain technical effects of one or more of the example embodiments disclosed herein are listed in the following.

The innovation underlying the embodiments disclosed hereby provides means to modulate surface properties of an implant to render the implant with a variety of functionalities. Surface properties can be modulated such, as make the implant to adhere tightly to bone to promote, for example, osteogenesis or fibrosis, to prevent osteogenesis of fibrosis, or to enable a possibility that adherence to a specific tissue may be instantaneously reduced. This enables provision of implants that are not surrounded by dense scar tissue (viz. provision of the implants that are exposed) and that are easier to replace in revision surgery in case of implant failure. The same technology can be utilized in surgical stents, such as cardiovascular, gastrointestinal, or urological stents, to facilitate their integration with surrounding tissue, while resisting the ingrowth of undesired tissue.

The medical implant structure, according to the embodiments, enables interfacing the implant with various cells and extracellular matrixes in flexible and versatile manner. Due to its dissimilar contact surfaces, the structure promotes contacts with different cell types. By altering these surface (s), the implant structure can thus be adapted to meet specific needs and requirements often posed by biological surroundings.

In present disclosure, materials with a layer thickness below 1 micrometer (μm) are referred to as "thin films".

In present disclosure, the terms "implant" and "endoprosthesis" are used interchangeably.

The expression "a number of" refers herein to any positive integer starting from one (1), e.g. to one, two, or three; whereas the expression "a plurality of" refers herein to any positive integer starting from two (2), e.g. to two, three, or four.

The terms "first" and "second" are not intended to denote any order, quantity, or importance, but rather are used to merely distinguish one element from another.

BRIEF DESCRIPTION OF THE DRAWINGS

The invention will now be described, by way of example only, with reference to the accompanying drawings, in which:

FIGS. 2 and 3 are schematically illustrated microscopic cross-sections of the interfacial layer of the medical implant structure, according to another embodiment, wherein FIG. 2 shows the substrate surface having the conformal coating selectively removed; and FIG. 3 shows the substrate surface of FIG. 2, having the conformal coating selectively removed, and being further deposited with the second, non-conformal coating at the places void of conformal coating.

DETAILED DESCRIPTION

Figure 1:
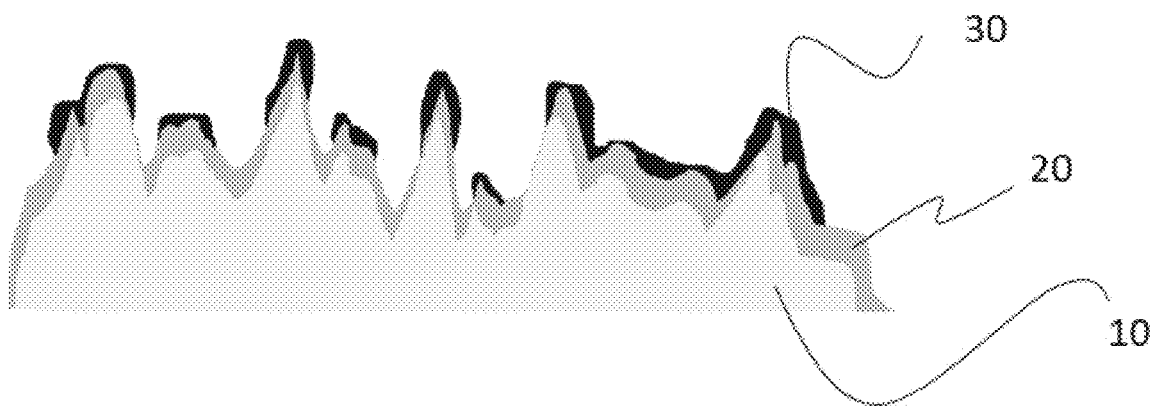
FIG. 1 is a schematically illustrated microscopic cross-section of an interfacial layer (with bone, for example) of a medical implant structure, according to an embodiment, which medical implant comprises a substrate surface provided with a conformal coating, followed by a non-conformal coating.

In an aspect, the invention concerns provision of a medical implant structure with surface-modulated properties.

The medical implant structure comprises a substrate 10 with at least a first surface and a second surface. The surfaces differ from one another with regard to at least one property in relation to a biological material surrounding said implant, such as tissues and cells.

The difference between the surfaces lies in ability thereof to establish, to maintain and/or to modulate an interaction of the implant structure with the surrounding biological material. Thus, at least the first surface and the second surface differ from one another in terms of their capability to establish-, to maintain and/or to modulate the at least one property descriptive of the interaction of said surfaces with the biological material and selected from the group consisting of adhesion, cell growth, biological activity, and toxicity.

The difference between said at least first and second surfaces can be further described as differences in capability to establish and/or to maintain an interface between the implant and the biological tissue (adhesion, cell growth). Biological activity is generally defined hereby as a capacity of the structure to attain and to module a specific biological effect with regard to a target (a biological tissue). For example, the surfaces rendered with a predetermined biological activity can promote or hinder osseointegration of the implants into the bone and/or promote or hinder bone tissue formation around the implant.

All above mentioned properties are linked together by a concept of biocompatibility of the implant. Biocompatibility is defined as an ability of the implant to exhibit an appropriate host response in relation to the surrounding biological tissue. By appropriate host response it is generally understood that the implant does not release any toxic elements or particles, neither it induces excessive immune, inflammatory and/or fibrogenic responses and/or disrupts or damages adjacent biological material and/or structures.

Therefore, by careful selection of the surface materials, any one of the above mentioned properties can be efficiently adjusted/modified, and biocompatibility of the implant can be regulated with high precision.

In the structure, the first surface and the second surface are disposed essentially on top of each other. A stack comprising more than two surfaces can be established in similar manner.

The at least one surface in the medical implant structure is established by a coating deposited by a method of chemical deposition in gaseous (vapour) phase, such as Atomic Layer Deposition (ALD) or, alternatively, Chemical Vapour Deposition (CVD). In some instances, the coating comprises at least one metal compound.

It is preferred that said at least one coating is a conformal coating.

The basics of an ALD growth mechanism are known to a skilled person. ALD is a special chemical deposition method based on the sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness. In some instances, Chemical Vapour Deposition (CVD) may be utilized.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: MLD (Molecular Layer Deposition), plasma-assisted ALD, for example PEALD (Plasma Enhanced Atomic Layer Deposition) and photon-enhanced Atomic Layer Deposition (known also as photo-ALD or flash enhanced ALD). The process can also be an etching process, one example of which being an ALE process. It should be noted that with PEALD and photon-enhanced ALD, the additive treatment can be limited to the surfaces visible to the radiation source.

ALD is based on alternating self-saturative surface reactions, wherein different reactants (precursors) provided as chemical compounds or elements in a nonreactive (inert) gaseous carrier are sequentially pulsed into a reaction space accommodating a substrate. Deposition of a reactant is followed by purging the substrate by inert gas. Conventional ALD deposition cycle proceeds in two half-reactions (pulse A-purge A; pulse B-purge B), whereby a layer of material is formed in a self-limiting (self-saturating) manner, typically being 0.05-0.2 nm thick. Typical substrate exposure time for each precursor ranges within 0.01-1 seconds.

Pulse A comprises a first precursor in a gaseous phase (first precursor vapor) and pulse B comprises a second precursor in a gaseous phase (second precursor vapor). Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapor pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

FIG. 1 shows a microscopic cross-section of an exemplary configuration of the medical implant structure with an interfacial layer with surrounding tissue, such as bone tissue, for example. The substrate 10 can be made of any suitable material, such as metals and metal alloys, ceramics, polymeric materials, composites, and combinations thereof. Prior to depositing the coating layer(s), the substrate 10 can undergo a pretreatment by mechanical or chemical means, such as etching, oxidation, and the like.

The first surface is established by a first coating layer 20 deposited over the substrate 10. It is preferred that the coating layer 20 forming the first surface (hereby, the surface deposited on the substrate 10) is established by a conformal coating (produces full, hole-free coverage across the entire substrate surface).

In some configurations, the conformal coating layer 20 is established as an Atomic Layer Deposition (ALD) coating layer. For clarity, the coating layer 20 can comprise at least one sublayer formed during one ALD deposition cycle. Typically, the coating layer 20 comprises a number of sublayers, each sublayer formed during one ALD deposition cycle.

The second surface is established by a second coating layer 30 deposited over the first coating layer 20.

For clarity, the terms "first surface" and "second surface" are used, in present disclosure, interchangeably with the terms "first coating layer" and "second coating layer", accordingly.

In configuration of FIG. 1, the second coating layer 30 deposited over the conformal coating layer 20 is a non-conformal coating. Such non-conformal layer 30 can be produced, on the top of the conformal layer, by photon-enhanced ALD, plasma-enhanced ALD- or CVD-methods, or by any non-vacuum deposition process.

In configuration illustrated by FIG. 1, the first surface and the second surface are thus disposed essentially on top of each other.

As can be observed from FIG. 1, when the substrate 10 forming the implant structure has essentially porous and/or irregular surface, the conformal coating 20 produces a (first) surface to uniformly coat all these irregularities. The non-conformal coating 30 applied thereafter to produce the second surface, is deposited only onto some portions of said first surface, hereby, onto the most protruding portions, while recessed parts remain uncoated. As a result, an implant structure is produced having two surfaces with different functionalities exposed to surrounding tissue.

The surface ratio between the first- and second surfaces can vary depending on substrate profile and reaction conditions (in particular, when depositing the second coating layer 30). Variations in surface profile derive, in turn, from surface- and/or material properties, such as texture, porosity, and/or presence of any irregular features, e.g. relief profiles, on the surface of the implant structure.

In an exemplary configuration, the conformal coating layer 20 can be hafnium (IV) oxide ($HfO_2$). Hafnium oxide possesses, among others, antimicrobial properties. In some instances, the conformal layer 20 can be provided as a laminate layer comprising a number of compounds.

Figure 2:
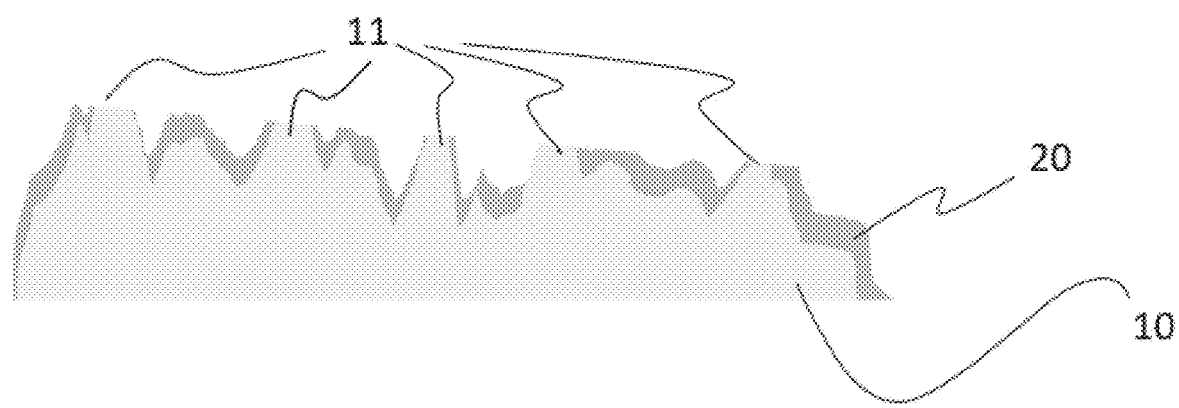
Figure 3:
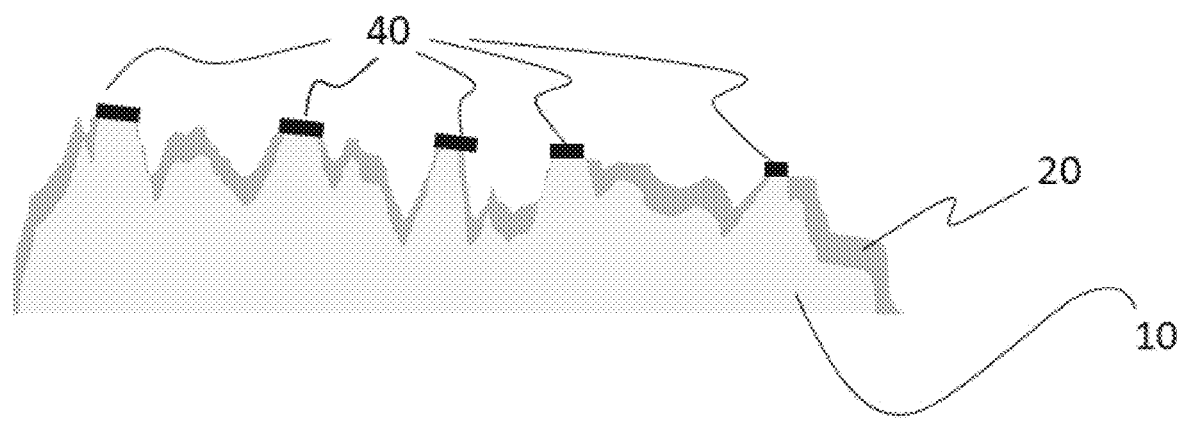

FIGS. 1-3 (schematically illustrated microscopic cross-sections) demonstrate that the interfacial layer is non-planar. The interface thus formed between the implant and the adjacent tissue is non-uniform. This is because formation of such interface generally implies provision of porous biological material thereat, such as bone. In some instances, the substrate 10 can be biological tissue, such as bone.

FIGS. 2 and 3 illustrate formation of the medical implant structure with an interfacial layer to surrounding tissue, such as bone tissue, according to another configuration. FIG. 2 thus shows formation of the interfacial layer of the implant structure by depositing the conformal coating layer 20 on the substrate 10 followed by selective removal of said conformal coating. Selective removal of conformal coating is naturally implemented at the highest points 11 (so called "peaks") of the substrate. Removal can be done by etching or any other abrasive technique.

It should be clear to those skilled in the art that the conformal coating 20 can be selectively removed from any portions of the substrate, i.e. when the substrate is uniform (contains no prominent "peaks") by utilizing appropriate selective material masking/removal technologies.

The substrate surface 10 void of any coating layer (as shown on FIG. 2) can be oxidized. Oxidation may be performed by an oxidation chemical or it may due to the ambient conditions (surrounding tissue, for example). Oxidation may be schematically depicted with an illustration of the non-conformal coating 40 on FIG. 3 (i.e. prior to formation of the layer coating 40, the surface void of the conformal "liner" coating 20 is oxidized in a manner illustrated for the coating 40 on FIG. 3).

After selective removal of the conformal layer 20 at some portions of the substrate 10, the surface of implant structure contains portions coated with the first coating 20 alternating with portions of exposed substrate 10. (FIG. 2). FIG. 3 illustrates further depositing of the implant structure surface with the second, non-conformal coating 40 at the places void of conformal coating 20. The second surface(s) created by the second coating 40 may partly overlap with the first surface(s) created by the first coating 20.

In exemplary configurations, the non-conformal coating layer 30, 40 can be titanium oxide ($TiO_2$), silicon oxide/silica ($SiO_2$), and the like.

FIGS. 2 and 3 thus illustrate a configuration, in which the substrate is substantially processed, e.g. by grinding processes, to remove the higher surface features (viz. selective removal of conformal coating 20 and, optionally, the substrate underneath said coating), revealing the substrate areas 11 of the implant. The same can be implemented also with a patterning process, such as etching or laser scribing. In particular, the etching process described hereinabove allows for removal of strictly conformal coating material 20 from the topmost areas ("peaks" 11), but not the substrate material underneath.

Further coating process for applying the second coating layer 40 to at least partly cover the opened surfaces 11 is advantageously implemented by means of area- and/or substrate selective chemical deposition processes, but not excluding the non-vacuum processes. This process can be also conformal oxidation, which affects only the exposed areas to create the coating 40 only on said exposed areas.

Hence, whereas FIG. 1 depicts formation of the non-conformal coating 30 over the conformal layer 20 (predetermined areas on said conformal layer); FIG. 3 depicts formation of the non-conformal coating 40 essentially over the exposed substrate 10 (in present example, over the peak areas 11), at which the conformal layer 20 has been removed. Thus, the implant structure can comprise the non-conformal layer 30 deposited onto the conformal layer 20 or it can comprise the non-conformal layer 40 deposited essentially onto the substrate surface 10.

The implant structure thus comprises at least one surface established by a conformal coating layer 20 and at least one surface established by a non-conformal coating layer 30, 40. Said at least one surface established by the non-conformal coating layer 30 can be deposited over the surface established by the conformal coating layer 20. Alternatively, said least one surface established by the non-conformal coating layer 40 can be deposited over the substrate surface 10.

In the embodiments described above, a generally non-planar substrate (implant) surface 10, such as an etched surface, is coated with conformal coating 20, such as ALD. The external surface is further applied with a different coating material 30, 40 (as a non-conformal coating layer).

Once the first- and the second coatings are applied, the process may continue with further deposition optionally combined with etching to selectively apply a third- and more surface coatings, as desired. The third coating (not shown) may be used to selectively coat e.g. cavities.

The medical implant structure, according to any embodiment described above is preferably configured as a three-dimensional shaped body to engage and integrate with bone tissue. The implant structure can be configured as a dental implant.

In embodiments, the structure is configured as a joint implant, in particular the joint implant used in replacement surgery. By way of example and not limitation, the structure can be provided as an artificial joint for any one of hip, knee, shoulder, elbow and ankle, or as an interphalangeal joint. The implant structure can be configured as a joint implant with fixed- or mobile (e.g. rotating) bearing components.

In another aspect, the invention pertains to provision of a joint implant comprising the medical implant structure according to the embodiments.

The implant structure disclosed hereby can be applied in most beneficial manner in joint (endo)prostheses, in where uncontrollable growth of connective tissue around the prosthesis is a problem. In some instances, when said prosthesis undergoes a revision procedure, it may be very hard to reach the prosthesis and to separate it from surrounding bone tissue.

In conventional processes of implant coating, enlarging the surface area to be coated is typically achieved by different methods, such as adding a mesh to the surface, annealing metal powder, stamping (embossing), electroplating or subtractive processes, such as etching, which can be patterned or conformal. All these procedures increase the implant adhesion to bone by stimulating osteogenesis. However, in case of joint implants, as well as orthopedic nails and plates, the abovementioned procedures are not efficient since they mainly promote formation of an interface only between the implant and bone cells. However, in particular for joint implants, facilitating formation of the interface with multiple different cell types, depending on the application, may be beneficial. Such interface can enable or at least promote adhesion of the implant structure, in addition to bone cells, to myocytes, fibrocytes, smooth muscle cells, endothelial cells, epithelial cells and neurons, depending on specific requirement. Furthermore, the interface with bone tissue can be configured removable/detachable.

The implant structure can be further rendered with such interfacial surface that the predetermined portions of said interface, such as cavities or recesses formed by (open) pores, for example, will have a different surface than the portions formed by a surface essentially between/above these cavities (pores). Thus, the internal surface(s) of said pores can be deposited with a coating preventing growth of harmful microorganisms, such as bacteria and/or fungi. The implant structure may thus comprise the at least one coating layer configured as an antimicrobial or antibacterial coating layer.

In an aspect, the invention further pertains to a method of manufacturing a medical implant structure, according to the embodiments. The method comprises obtaining a substrate 10 and depositing at least one conformal coating layer 20 onto said substrate. The conformal coating layer 20 is preferably established by Atomic Layer Deposition (ALD). The method further comprises depositing a non-conformal coating layer 30 over the surface established by the conformal coating layer 20.

In some configurations, the method comprises removal of at least a part of the conformal coating layer 20 deposited over the substrate 10, whereby at least a part of the substrate surface 10 is rendered exposed. Removal can be done be abrasive- or patterning/etching processes. Thereafter, a non-conformal coating layer 40 is deposited over the exposed substrate surface 10.

It shall be appreciated by those skilled in the art that the embodiments set forth in the present disclosure may be adapted and combined as desired. The disclosure is thus intended to encompass any possible modifications of the device and the deposition method, recognizable by those of ordinary skill in the art, within a scope of appended claims.

The invention claimed is:

1. A medical implant structure comprising: a substrate with an interfacial layer to surrounding tissue formed by at least a first coating layer and a second coating layer, the first and second coating layers differing from one another with regard to at least one property in relation to biological material, wherein the substrate has an essentially porous and irregular surface, the substrate including recessed parts and most-protruding portions, wherein the first coating layer is a conformal coating that uniformly coats irregularities of the substrate, and wherein the second coating layer is a topmost, non-conformal coating deposited onto the most-protruding portions of said substrate surface, wherein said most-protruding portions of said substrate surface on which the second coating layer is deposited is void of said first coating layer, and wherein the second coating layer does not coat the recessed parts of the substrate.

2. The medical implant structure of claim 1, in which the first coating layer and the second coating layer differ from one another in terms of at least one property selected from the group consisting of adhesion, cell growth, biological activity, and toxicity.

3. The medical implant structure of claim 1, in which the first coating layer and the second coating layer are disposed essentially on top of each other.

4. The medical implant structure of claim 1, wherein the first coating layer is deposited over and coats all the irregularities of the substrate except the most-protruding portions of said substrate on which the second coating layer is deposited.

5. The medical implant structure of claim 1, wherein the first coating layer comprises hafnium (IV) oxide.

6. The medical implant structure of claim 1, in which the first coating layer is an Atomic Layer Deposition (ALD) layer.

7. The medical implant structure of claim 1, wherein said most-protruding portions of said substrate surface on which the second coating layer is deposited is an oxidized surface void of said first coating layer.

8. A joint implant comprising the medical implant structure as defined in claim 1.

9. A method of manufacturing a medical implant structure as defined in claim 1, wherein said first coating layer is established by an Atomic Layer Deposition (ALD) layer.

10. The method of claim 9, further comprising removal of at least a part of the first coating layer deposited over the substrate, whereby at least a part of the substrate surface is rendered exposed, and depositing the second coating layer over the exposed substrate surface.

* * * * *